United States Patent [19]
Edwards

[11] 3,950,999
[45] Apr. 20, 1976

[54] SAMPLING APPARATUS FOR LIQUIDS

[76] Inventor: Vernon T. Edwards, 797 Babbitt Road, Cleveland, Ohio 44123

[22] Filed: Aug. 6, 1975

[21] Appl. No.: 602,282

[52] U.S. Cl............................................. 73/425.4 R
[51] Int. Cl.²......................................... G01N 1/12
[58] Field of Search.......... 73/425.2, 425.4 R, 425.6

[56] References Cited
UNITED STATES PATENTS

| | | | |
|---|---|---|---|
| 2,488,486 | 11/1949 | Worzel | 73/425.2 |
| 3,277,723 | 10/1966 | Bodman | 73/425.4 R |

*Primary Examiner*—S. Clement Swisher
*Attorney, Agent, or Firm*—Wesley B. Taylor

[57] ABSTRACT

Sampling apparatus is disclosed for liquids, such as water, including cup-shaped members fixed to one another in partial telescoping relation with their closed end portions opposed. A piston disposed within the inner cup-shaped member contacts its walls and is adapted for reversible travel longitudinally of that member. The apparatus carries sampling, one-way valve means adapted to open only for intake. Conduit means connects the one-way valve means to the interior of the inner cup-shaped member between its closed end portion and the piston. In operation, the piston forces a liquid from the sampling area within the telescoping cup-shaped members while simultaneously refilling the evacuated area, due to the resulting reduced pressure, with the liquid to be sampled.

18 Claims, 6 Drawing Figures

SAMPLING APPARATUS FOR LIQUIDS

BACKGROUND OF THE INVENTION

The present invention relates generally to oceanographic apparatus and, more particularly, to a water sampler for obtaining uncontaminated samples of near-bottom liquids for analytical studies. The sampling apparatus is adapted to be lowered into lakes, rivers, and the like for the purpose of collecting samples of water which can then be examined with regard to their oxygen content as well as the content of other substances suspended or dissolved therein. The samples obtained must be of sufficient volume and free of contamination to represent reliably the water composition being sampled. Also, the need for aseptic sampling has long been recognized in bacteriological studies.

The study of near-bottom water in bodies of water like lakes and oceans has become quite important in recent years due to an increased understanding of the unique chemical and biological reactions which take place at the mud-water interface. Samples of water taken from this zone generally contain chemical and biological species which are changed or diluted beyond detection as they are mixed with the entire body of water. Since this water has considerable biological and health related impacts, it is desirable to sample and analyze the water lying quite close to the bottom, for example, within one or two inches of the bottom.

In the past, samples had been taken close to a bottom of a body of water by using sampling apparatus designed to draw water at any particular depth and by suspending such apparatus near the bottom to obtain the desired sample. This led to uncertainty of actual sampling depths, since sampling personnel could not actually observe the sampler in operation. This practice also led to disturbing the bottom by impact by the sampler with the resultant taking of a non-representative sample. Near-bottom samples have also been taken using a pump and hose, but this system has the same inherent drawbacks.

SUMMARY OF THE INVENTION

A primary object of the present invention is to provide sampling apparatus for obtaining for analytical studies an uncontaminated sample of liquid, such as water, under near-bottom conditions of relatively large bodies of the liquid.

Another object is to provide sampling apparatus which avoids or minimizes disturbance of the bottom of the liquid body during a sampling operation.

A further object is to provide sampling apparatus which is able to obtain a sample of near-bottom liquid at a pre-set distance from the bottom.

A still further object is to provide sampling apparatus which operates automatically without a mechanical surface-released messenger or electric apparatus.

In one form, the present apparatus comprises partially telescoping cup-shaped members, such as tubular members, having their opposed ends closed and fixed relatively to each other in such telescoping relation. One of the tubes is disposed within the other. A piston member within the inner tube contacts the walls thereof and is adapted for reciprocable longitudinal movement with respect to the inner tube. The outer tube has sampling one-way valve means adjacent its closed end adapted to open for intake only, while conduit means connects the one-way valve means to the interior of the inner tube between its closed end and the piston member.

Preferably, the inner and outer tubes define therebetween an intervening annular area, and the conduit means passes through the intervening area to reach the interior of the inner tube as described.

The apparatus may be fitted with laterally extending fins for stabilization purposes, and the apparatus may have elevating pins to position the sampler somewhat above the bottom of the body of liquid in which the sample is taken.

DESCRIPTION OF THE PREFERRED EMBODIMENT

Figure 1:
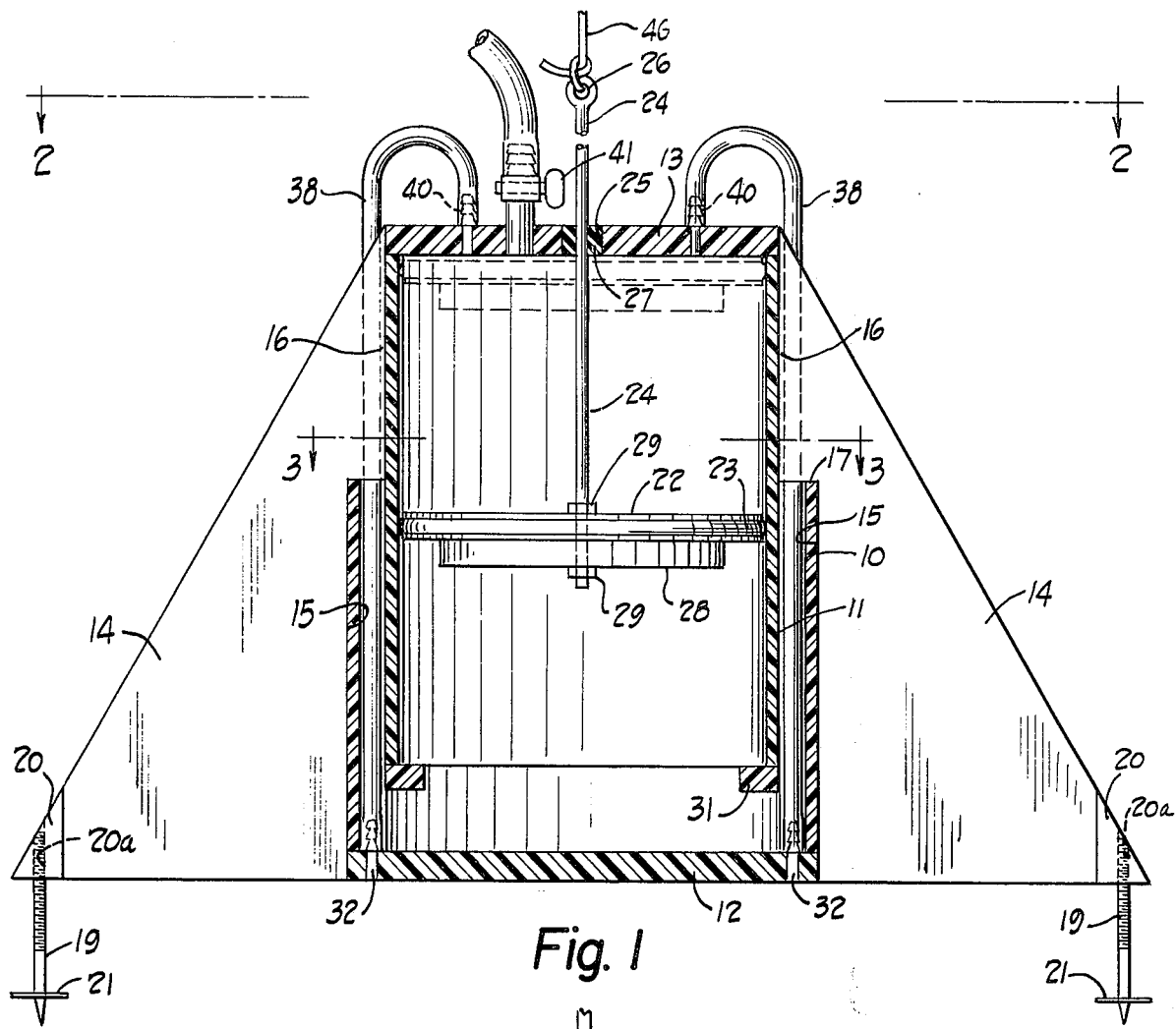
FIG. 1 is a vertical section of one embodiment of the invention taken on line 1—1 of FIG. 2.

Referring to the drawing, the illustrated embodiment includes a pair of cup-shaped members fixed to one another in partial telescoping relation as defined by an outer tube 10 and an inner tube 11 having their opposed ends closed by plates 12 and 13, respectfully. Tubes 10 and 11 may be composed of any suitable material but preferably comprise a synthetic resinous organic material and especially thermoplastic materials like polyethylene, polypropylene, polymethacrylate, nylon, and the like. The thermoplastic character of such materials enable parts fabricated therefrom to be fixed relatively to each other by conventional heat sealing.

Figure 2:
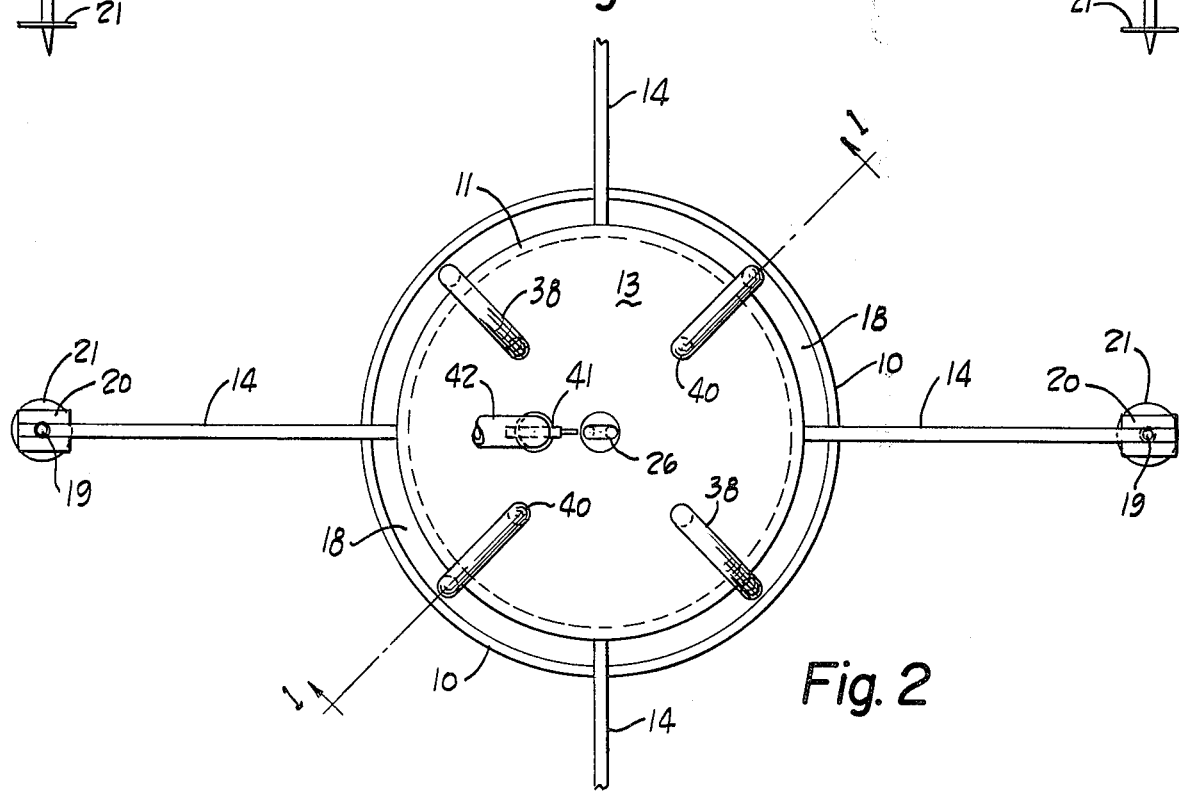
FIG. 2 is a top plan view of FIG. 1 with parts of fins broken away.
Figure 3:
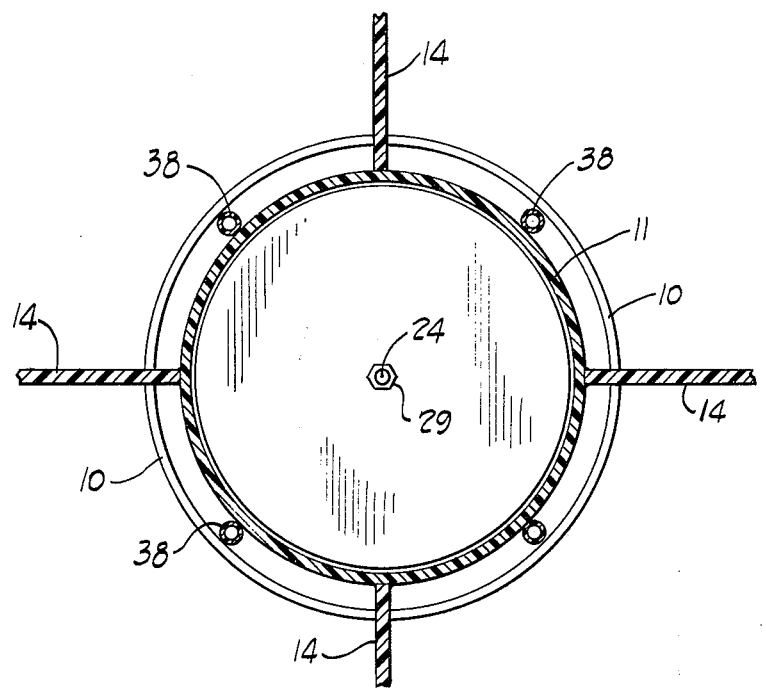
FIG. 3 is a section of FIG. 1 on the line 3—3.

For example, in the illustrated embodiment, tubes 10 and 11 are fixed relatively to one another by four laterally extending fins 14 spaced 90° apart with respect to a central, longitudinal axis passing concentrically through the tubes. Fins 14, which may be composed of the same material as tubes 10 and 11, are essentially in the form of right triangles with the normally vertically disposed side having a cut-away portion 15 so as to butt against the outer tube 10 of greater diameter and leave a radially inwardly projecting edge portion 16 of sufficient length to reach and contact that section of inner tube 11 of smaller diameter which extends above an edge 17 of tube 10. Since cut-away portion 15 and edge portion 16 of each fin 14 contacts outer and inner tubes, respectfully, as described, the touching parts of these thermoplastic materials may be securely joined to one another by heat sealing in a manner known in the art. The telescoping tubes 10 and 11 are thus secured to one another, leaving an intervening, annular area 18 therebetween (FIG. 2).

The fins stabilize the sampling apparatus as by inhibiting rotation about a central longitudinal axis or swinging during descent or ascent in a body of liquid. When the apparatus nears or reaches a bottom of a liquid body, it is helpful to elevate the apparatus somewhat above the bottom. In the present apparatus this is accomplished by providing elevating means on the fins which may take the form of pins 19 secured in the enlarged, exposed triangular tips 20 of the fins. Each pin 19 may have a fixed button 21 which, upon immersion into a bed at the bottom of a liquid body, serves to increase the anchoring hold of pin 19. Preferably, pins 19 are threaded and may be vertically adjusted by turning in mating threaded passages 20a in enlarged tips 20. This varies the sampling height for the apparatus.

A piston 22 disposed within inner tube 11 is adapted for reversible travel longitudinally of the tube. The piston has a circumferential groove in which an O-ring 23 conventionally seats and makes a substantially liquid-tight seal with the inner walls of inner tube 11. A piston rod 24 connected to piston 22 passes through an opening 25 in end plate 13 and terminates in suitable connecting means, such as an eyelet 26, to which a cable, cord, line, or the like may be conventionally secured. Opening 25 contains an elastomeric, apertured plug 27 to prevent unwanted liquid entry into inner tube 11 around piston rod 24. While there is substantially the same hydrostatic head on both sides of piston 22, it should be sufficiently weighted to overcome the frictional drag of O-ring 23 against the inner walls of inner tube 11 and any resistance to water flow through tubing. This can be accomplished, for example, by a heavy metallic disc 28 which is secured against piston 22 (FIG. 1) by two nuts 29 straddling the piston and disc and engaging threaded portions on piston rod 24.

Preferably, inner tube 11 has retaining means to limit longitudinal travel of piston 22 away from end plate 13. In the illustrated embodiment, this takes the form of a radial, inwardly turned flange 31 fixed to the tube which prevents piston 22 from passing beyond the open end of tube 11.

Figure 4:
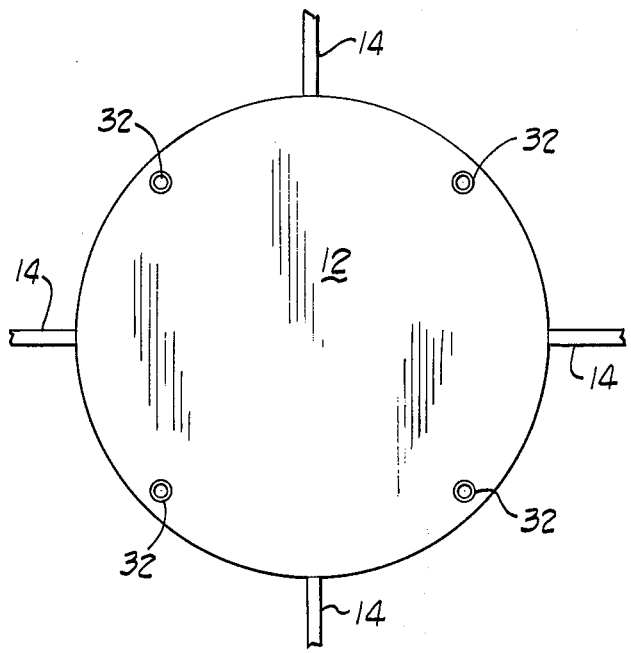
FIG. 4 is a bottom plan view of FIG. 1 with parts of the fins broken away and illustrates the sampling one-way valves.
Figure 5:
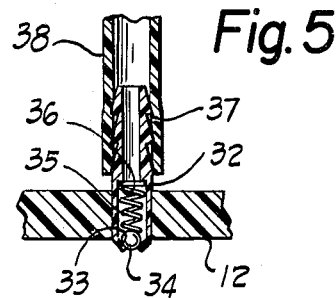
FIG. 5 is an enlarged, fragmentary side view of a one-way valve of FIG. 4.

As shown in FIG. 4, there are four, evenly spaced one-way or check valves 32 adapted to open for intake only. FIG. 5 illustrates one form such a valve may take. The valve is generally tubular and has a circular opening 33 in which a ball 34 seats to close the valve. A coiled spring 35 lodged between ball 34 and an inner shoulder portion 36 normally urges ball 34 to a closed position but opens to permit entry through the valve when the force of spring 35 is overcome by forces external to the valve. The upper portion of each valve 32 (as viewed in FIG. 5) has circumferential ridges 37 to grip better tubing such as rubber tubing 38.

Tubing 38 joins each of the one-way valves 32 to an open, two-way hose connector 40 fixed to and passing through end plate 13 in order to connect the one-way valves to the interior of inner tube 11 between piston 22 and end plate 13. In so joining valves 32 and connectors 40, tubing 38 passes through the intervening annular area 18 defined by telescoping tubes 10 and 11. End plate 13 may also carry a manually operated, pet cock valve 41 and connecting hose 42, the hose being attached when needed, through which to remove the sampled contents of inner tube 11 after a sampling operation has been completed.

Figure 6:
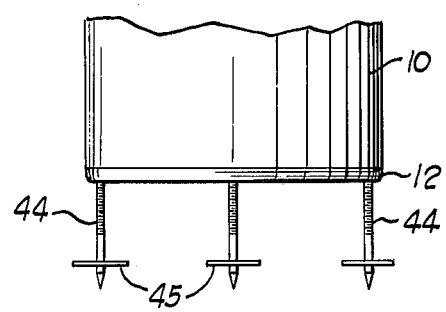
FIG. 6 is a fragmentary, lower view of a modified form of the present apparatus and shows an alternate placing of elevating pins.

FIG. 6 illustrates a modified mounting of elevating means and shows that fins are not essential. In this case, a lower end of tube 10 has four elevating pins 44, spaced 90° apart and secured to end plate 12 between the one-way valves 32. The pins may have anchoring buttons 45. If desired, pins 44 can be adjustably positioned to vary the mounting height by being threaded and engaging threaded openings which extend through plate 12 and into the lower extent of tube 10.

In use, a cable 46 attached to eyelet 26 of piston rod 24 lowers the sampling apparatus downward through a body of liquid. During this time, piston 22 is pulled upwardly by cable 46 relatively to inner tube 11 and against end plate 13, as shown in phantom in FIG. 1, such that the piston supports the weight of the apparatus. Also, during descent of the apparatus, fins 14 stabilize the apparatus against rotation and swinging. When the bottom of a body of liquid is reached or approached, elevating pins 19 bite into the bed of the body of liquid, without unduly disturbing it so as to contaminate the sampling operation, and further stabilize the apparatus against movement. Pins 19 also elevate plate 12 somewhat above the bottom of the body of liquid.

Since tubes 10 and 11 are open to the body of liquid as soon as they submerge, the tubes fill with ambient liquid. However, when the weight of the apparatus is borne by the bottom of the liquid body (or any other support), piston 22 leaves its position against end plate 13 and moves downwardly longitudinally of inner tube 11 until it strikes flange 31 which prevents further downward movement. This piston movement has a dual action. The piston stroke evacuates the unwanted liquid already within inner tube 11, pushing the liquid out between the two tubes 10 and 11 and through the intervening annular area 18. On the evacuation stroke of piston 22, it will be noted that the unwanted liquid is projected upwardly and away from the area where the sample is actually taken. Simultaneously, due to the reduced pressure within inner tube 11 and the hydrostatic pressure outside of the apparatus, one-way valves 32 are forced open, and the liquid desired to be sampled flows through valves 32 and tubing 38, hose connectors 40 into inner tube 11 to fill the volume between end plate 13 and the descended piston 22. Accordingly, an uncontaminated sample is entrapped within tube 11 at in situ pressures and temperatures for subsequent analytical studies.

After once reaching or approaching the bottom of a body of liquid, the operation as just described requires only a matter of seconds. Upon its completion, cable 46 is pulled upwardly to return the apparatus and its sample. Because the liquid is non-compressible, the sampled liquid actually bears the brunt of the lifting force applied through piston 22. Since valves 32 open only for entry, they are closed at this time and prevent loss of the sampled liquid. After the apparatus has been retreived, the sampled liquid is easily taken from the apparatus by opening pet cock valve 41, lifting piston 22 again by piston rod 24, and forcing the sampled liquid out through valve 41 and hose 42, attached for this purpose, to a suitable receptacle.

Although the foregoing describes a presently preferred embodiment, it is understood that the invention may be practiced in still other forms within the scope of the following claims.

I claim:

1. Apparatus of the class described including cup-shaped members fixed to one another in partial telescoping relation with their closed end portions opposed, a piston member disposed within the inner cup-shaped member in contact with the walls thereof and adapted for reversible travel longitudinally of said inner member, sampling one-way valve means carried by the apparatus and adapted to open for intake only, and conduit means connecting said one-way valve means to the interior of said inner cup-shaped member between its closed end portion and said piston member.

2. Apparatus of claim 1 having laterally extending fin means for stabilization.

3. Apparatus of claim 1 having elevating means adjacent the bottom thereof adapted to contact the bottom of a body of liquid in which a sample is to be taken.

4. Apparatus of claim 2 in which said fin means serves to fix said cup-shaped members relatively to each other.

5. Apparatus of claim 1 in which said inner cup-shaped member has retainer means to limit said longitudinal travel of the piston member away from the closed end portion of said inner cup-shaped member.

6. Apparatus of claim 1 in which said inner cup-shaped member has valve means to remove the sampled contents thereof.

7. Apparatus of claim 1 in which said cup-shaped members comprise a resinous synthetic material.

8. Apparatus of claim 1 in which the periphery of said piston member has sealing means to effect a substantial liquid-tight seal with the wall of said inner cup-shaped member.

9. Sampling apparatus adapted to sample a body of liquid at the bottom thereof, comprising: partially telescoping tubes having their opposed ends closed and fixed relatively to each other in such telescoping relation, one of said tubes being disposed within the other and defining therebetween an intervening annular area, a piston member disposed within the inner tube in contact with the walls thereof, means extending through the closed end of said inner tube for reciprocating the piston member longitudinally of said inner tube, sampling one-way valve means carried by the outer tube adjacent its closed end adapted to open for intake only, and conduit means disposed within said intervening annular area and connecting said one-way valve means to the interior of said inner tube between its closed end and said piston member.

10. Sampling apparatus of claim 9 in which said inner tube has valve means at its closed end, and said conduit means connects said one-way valve means to said first mentioned valve means.

11. Sampling apparatus of claim 9 having laterally extending fin means for stabilization.

12. Sampling apparatus of claim 9 in which said fin means serves to fix said partially telescoping tubes relatively to each other.

13. Sampling apparatus of claim 9 in which said inner tube has retainer means to limit said reciprocation of the piston member longitudinally away from the closed end of said inner member.

14. Sampling apparatus of claim 9 in which said inner tube has valve means to remove the sampled contents thereof.

15. Sampling apparatus of claim 9 in which the periphery of said piston member has sealing means to effect a substantially liquid-type seal with the wall of said inner tube.

16. Sampling apparatus of claim 9 in which said means extending through the closed end of the inner tube for reciprocating the piston member includes a piston rod.

17. Sampling apparatus of claim 9 in which said piston member is weighted.

18. Sampling apparatus of claim 9 in which the lower of said two tubes has adjustable elevating means adapted to elevate said apparatus with respect to said bottom of said body of liquid.

* * * * *